United States Patent [19]
Rouhof et al.

[11] Patent Number: 5,364,609
[45] Date of Patent: Nov. 15, 1994

[54] PROCESS FOR THE PREPARATION AND PROCESSING OF A HYDROXYLAMMONIUM SALT SOLUTION

[75] Inventors: Hendrikus J. H. Rouhof, Sittard; Godefridus M. Van Dortmont, Born; Michael W. M. Boesten, Beek (L.), all of Netherlands

[73] Assignee: DSM N.V., Netherlands

[21] Appl. No.: 76,904

[22] Filed: Jun. 15, 1993

[30] Foreign Application Priority Data

Jun. 16, 1992 [NL] Netherlands .......................... 9201064

[51] Int. Cl.$^5$ ............................................ C01B 21/20
[52] U.S. Cl. ...................... 423/387; 423/392; 564/259
[58] Field of Search ............... 423/387, 392, 403; 564/259

[56] References Cited

U.S. PATENT DOCUMENTS

| | | | |
|---|---|---|---|
| 3,514,254 | 5/1965 | de Rooij et al. | |
| 3,641,150 | 2/1972 | de Rooij | 564/259 |
| 3,655,760 | 4/1972 | de Rooij et al. | 564/259 |
| 3,701,809 | 10/1972 | de Rooij et al. | 564/259 |
| 3,940,442 | 2/1976 | de Rooij | 423/387 |
| 3,948,988 | 4/1976 | de Rooij | 564/259 |
| 4,122,153 | 10/1978 | Haasen et al. | 423/387 |
| 4,328,198 | 5/1982 | van de Moesdijk | 564/259 |
| 4,512,964 | 4/1985 | Vayenas et al. | 423/403 |
| 4,552,636 | 11/1985 | van den Brink et al. | 564/259 |

FOREIGN PATENT DOCUMENTS

| | | |
|---|---|---|
| 1279527 | 5/1972 | United Kingdom . |
| 1287302 | 8/1972 | United Kingdom . |
| 1287303 | 8/1972 | United Kingdom . |

*Primary Examiner*—Wayne Langel
*Attorney, Agent, or Firm*—Cushman, Darby & Cushman

[57] ABSTRACT

A process for the preparation and processing of a hydroxylammonium salt solution involves maintaining an aqueous acid reaction medium circulation between a hydroxylammonium salt synthesis zone and an oxime synthesis zone; continuously supplying nitrate ions or nitrogen oxides to be converted into nitrate, by way of nitrogen source for the formation of the hydroxylammonium salt, to the liquid being maintained in circulation; catalytically reducing the nitrate ions with hydrogen to obtain hydroxylamine; removing the ammonium ions, formed as a by-product in the reduction of the nitrate ions, by contacting the circulating liquid with a gas flow consisting of nitrogen oxides generated in catalytic combustion of ammonia. Advantageously, 0.01 to 5 wt. % of the nitrogen oxides formed in the combustion effect reduction of the ammonium ions to nitrogen, and the remainder of the nitrogen oxides are used for the preparation of nitric acid.

5 Claims, 2 Drawing Sheets

PROCESS FOR THE PREPARATION AND PROCESSING OF A HYDROXYLAMMONIUM SALT SOLUTION

FIELD OF THE INVENTION

The present invention relates to a process for the preparation and processing of a hydroxylammonium salt solution. In the present invention an aqueous acid reaction medium is kept in circulation between a hydroxylammonium salt synthesis zone and an oxime synthesis zone. Nitrate ions or nitrogen oxides to be converted into nitrate are continuously supplied to the liquid being kept in circulation, by way of nitrogen source for the formation of the hydroxylammonium salt. The nitrate ions are catalytically reduced with hydrogen to hydroxylamine. Ammonium ions, formed as a by-product in the reduction of the nitrate ions, are removed by conversion with nitrogen oxides.

In a process according to the invention, cyclohexanone oxime is produced using hydroxylammonium salt and cyclohexanone as starting materials. The oxime can, in turn, be used as a starting material for the preparation of $\epsilon$-caprolactam.

BACKGROUND OF THE INVENTION

A process is described in United Kingdom 1,287,303, in which circulation of a buffered solution between a zone wherein hydroxylammonium salt is formed and a zone wherein cyclohexanone oxime is formed. The chemical reactions that take place in the different zones are represented by reaction equations 1-3, as follows.

1) Preparation of the hydroxylammonium salt:

$$2 H_3PO_4 + NO_3^- + 3 H_2 \rightarrow NH_3OH^+ + 2 H_2PO_4^- + 2 H_2O$$

2) Preparation of the oxime:

$$NH_3OH^+ + 2 H_2PO_4^- + 2 H_2O + H=O \rightarrow H=N-OH + H_3PO_4 + H_2PO_4^- + 3 H_2O$$

3) Supply of $HNO_3$ to make up the depletion of the source of nitrate ions after removal of the oxime formed:

$$H_2PO_4^- + HNO_3 \rightarrow H_3PO_4 + NO_3^-$$

The depletion of the nitrate ion source is made up by absorption into the circulating reaction mixture of gases containing nitrogen oxides, resulting in the formation of nitric acid. Directly supplying nitric acid to the reaction mixture is also possible. It is further possible to combine the absorption of nitrogen oxides and the supplying of nitric acid. When the nitric acid or the nitrogen oxides to be converted into nitrate have been added, the reaction mixture, has the same theoretical composition after the removal of water as the initial starting solution started from for the preparation of the hydroxylammonium salt. Furthermore, however, in the step involving the preparation of the hydroxylammonium salt, a quantity of ammonium ions is formed because the hydrogenation is not fully selective. In order to avoid an accumulation of ammonium ions in a continuous circulation process, the ammonium ions formed are converted by means of gases containing nitrogen oxides in accordance with the following reaction:

$$2 NH_4^+ + NO + NO_2 \rightarrow 2 N_2 + 3 H_2O + 2 H^+$$

This process is also referred to as the HPO (hydroxylamine phosphate oxime) process in the literature such as, Damme et al., Chemical Engineering, (Jul. 10, 1972), pages 54–55, the disclosure of which is incorporated herein by reference.

In the HPO process, the nitrogen oxides (nitrogen monoxide+nitrogen dioxide) are obtained by methods well known in the art by forced ammonia combustion, whereby ammonia and air are converted into nitrogen oxides and water. Part of the nitrogen monoxide formed is oxidized to nitrogen dioxide by means of secondary air, that is, air other than the stoichiometric amount of air. The HPO-ammonia combustion process is disadvantageous in that it has a small capacity, and therefore the efficiency of the ammonia combustion is lower than the efficiency of the ammonia combustion of a normal nitric acid production process, which is, in general, only 91% (on a per mol basis).

Another disadvantage is the great amount of process equipment which is needed for the nitric acid and nitrogen oxide preparation.

A further disadvantage is the environmental impact of the release of nitrogen oxides containing gases of a normal HPO process. It is quite expensive to build a nitrogen separation unit for such a small ammonia combustion. Thus, there is a need in the art to overcome this problem.

SUMMARY OF THE INVENTION

The present invention relates to a process for producing hydroxylammonium salt solution, wherein an aqueous acid reaction medium which contains ammonia ions is continuously circulated between an hydroxylammonium salt synthesis zone and an oxime synthesis zone comprising the steps of:

(i) continuously supplying nitrate ions or nitrogen oxides to be converted into nitrate by a nitrogen source to the aqueous acid reaction medium for formation of hydroxylammonium salt;

(ii) catalytically reducing the nitrate ions with molecular hydrogen to hydroxylamine, wherein ammonium ions are formed as a by-product in reduction of the nitrate ions;

(iii) removing the ammonium ions by conversion with nitrogen oxides;

(iv) contacting the aqueous acid reaction liquid with a gas flow containing nitrogen oxides generated in catalytic combustion of ammonia;

(v) converting ammonium ions into nitrogen utilizing 0.01 to 5 wt. % of the nitrogen oxides formed in the catalytic combustion of ammonia;

(vi) utilizing remaining nitrogen oxide containing gas flow for preparation of nitric acid.

The preparation of the hydroxylammonium salt is catalyzed heterogeneously. The catalyst consists mostly of a metal from the platinum metal group, for instance, Pd or Pd+Pt, as active component on a carrier material such as carbon. Further, minor quantities of other components can be added as an activator. Examples of suitable components include Cu, Ag, Cd, Hg, Ga, In, Tl, Ge, Sn, Pb, As, Sb or Bi.

Non-converted nitrogen oxides of the nitrogen oxide containing gas flow are recycled into a process for nitric acid production, and the process for nitric acid production can be the source for the nitrate ions used for formation of hydroxylammonium salt.

Preparation of nitric acid is achieved by a process having a capacity of 200 to 750 kt $HNO_3$/year (dry).

Ammonium ions may be converted into nitrogen 0.5-3 wt. % of the nitrogen oxides formed in the combustion.

DETAILED DESCRIPTION OF THE INVENTION

The present invention relates to a process for producing hydroxylammonium salt solution, wherein an aqueous acid reaction medium which contains ammonia ions is continuously circulated between an hydroxylammonium salt synthesis zone and an oxime synthesis zone comprising the steps of:

(i) continuously supplying nitrate ions or nitrogen oxides to be converted into nitrate by a nitrogen source to the aqueous acid reaction medium for formation of hydroxylammonium salt;

(ii) catalytically reducing the nitrate ions with molecular hydrogen to hydroxylamine, wherein ammonium ions are formed as a by-product in reduction of the nitrate ions;

(iii) removing the ammonium ions by conversion with nitrogen oxides;

(iv) contacting the aqueous acid reaction liquid with a gas flow containing nitrogen oxides generated in catalytic combustion of ammonia;

(v) converting ammonium ions into nitrogen utilizing 0.01 to 5 wt. % of the nitrogen oxides formed in catalytic combustion of ammonia;

(vi) utilizing remaining nitrogen oxide containing gas flow for preparation of nitric acid.

In the present process, improved efficiency of ammonia combustion is achieved because the circulating liquid containing ammonia ions is in contact with a gas flow containing nitrogen oxides generated in catalytic combustion of ammonia where 0.01 to 5 wt. % of the nitrogen oxides formed in the combustion is used to convert ammonium ions into nitrogen, and the remainder of the nitrogen oxide containing gas flow is used for the preparation of nitric acid.

Preferably, 0.5-3 wt. % of the nitrogen oxides is used to convert ammonium ions into nitrogen.

The ratio between the quantity of nitrogen oxides that are used to convert ammonium oxides into nitrogen and the quantity that is used for the preparation of the hydroxylammonium salt solution generally ranges between 5:95 and 25:75.

The present invention makes it possible to use a single ammonia combustion plant for concurrently (1) supplying nitrogen oxide for use in the preparation of a hydroxylammonium salt solution in a commercial HPO process, and (2) the preparation of nitric acid in a commercial nitric acid production process. In this context, a commercial nitric acid production process means a process with a capacity of 200 to 750 kt $HNO_3$/year (dry). In general, a commercial HPO process has a nitric acid consumption of 50 to 110 kt/$HNO_3$/year (dry). This nitric acid consumption corresponds to the total of nitric acid and nitrogen oxides (to be converted into nitric acid) that is consumed in an HPO process.

The present invention is advantageous because the ammonia combustion can be carried out on such a scale that the efficiency of the ammonia combustion will be considerably higher compared to when ammonia combustion is carried out only for use in the HPO process.

Figure 1:
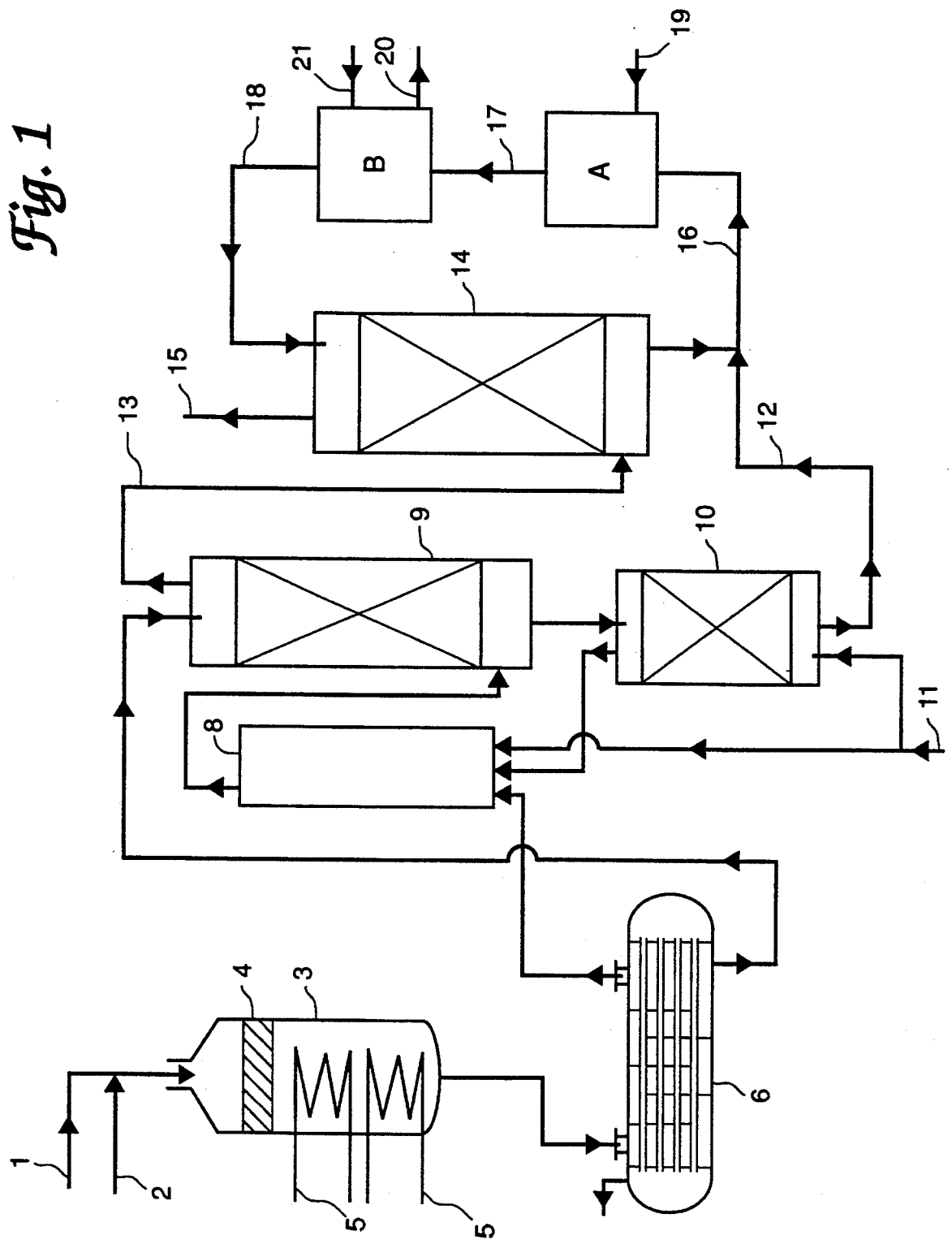
FIG. 1 shows a block diagram of a process according to the prior art.

United Kingdom 1,287,303, the disclosure of which is incorporated herein by reference, describes how and with what process steps the flow containing nitrogen oxide and the nitric acid are produced in an HPO process. As described therein, a great deal of equipment is required for such a process, such as an ammonia combustion facility, hot gas condenser, oxidation column, absorption system and stripping column (such as is shown in FIG. 1). In addition to the steps enumerated in United Kingdom 1,287,303, steps for the purification of nitrogen containing gas flows (such as gas flow 15 in FIG. 1) required in order to meet current environmental standards, which means that in practice the number of process steps will be even greater. For instance, additional steps for the purification of nitrogen oxide containing gas streams leaving the HPO process must be added to conform to environmental requirements.

In distinct contrast to United Kingdom 1,287,303, an advantage in the present invention is that the number of process steps in the HPO process can be reduced. For example, according to the present invention, the number of times that the ammonia combustion facility has to be put on and taken off stream (i.e., start and stop the ammonia combustion process) will be fewer than in the process described by the United Kingdom patent.

Typically, when the ammonia combustion facility for an HPO process has to be taken off stream, the HPO process will be off stream as well. Nitric acid and/or nitrogen oxide are prepared in a nitric acid plant with a capacity of 200–750 kt $HNO_3$/year. However, the amount of nitric acid and/or nitrogen oxide needed for the HPO process is significantly smaller (50–110 kt $HNO_3$/year). Therefore, it is not necessary to stop production at the nitric acid plant every time the HPO plant is taken off stream.

In the present invention there is no need for both an ammonia combustion facility for the HPO process and a separate ammonia combustion facility for nitric acid production. Because an HPO plant is taken off and put on stream more frequently than a nitric acid plant is, it is clear that in the process according to the invention the ammonia combustion of the nitric acid plant will be taken off and put on stream fewer times than the ammonia combustion of an HPO process. Every time that the ammonia combustion is started, environmental problems (such as release of nitrogen oxide) occurs. Therefore, it is advantageous to minimize the number of times ammonia combustion is stopped and started. Consequently, the environmental impact of putting on and taking off stream the ammonia combustion facility will be reduced by the process of the invention.

One embodiment of the invention involves a process wherein part of the flow containing nitrogen oxide from a nitric acid production process is used for the destruction of ammonium ions later in a consecutive step. The nitrogen oxides are supplied in this embodiment by a nitric acid production process (for instance, 200–750 kt $NHO_3$/year), in which a part (0.01–5.0 wt. %) of the nitrogen oxides are used in the HPO process for converting ammonium into nitrogen. Part of the remaining nitrogen oxide is used for the on-the-spot preparation of hydroxylammonium salt. The remaining nitrogen oxides, being the largest part of the nitrogen oxides produced by the ammonia combustion, is used to make nitric acid in the nitric acid production process (for instance, 200–750 kt NHO$_3$/year). The advantage is that no ammonia combustion is needed in the HPO process because the nitrogen oxides are prepared in a nitric acid production process. Thus, in addition to an ammonium ion destruction step, a number of absorption columns are needed for the on-the-spot HPO nitric acid production.

In order to avoid the need to use extra absorption columns, the following embodiment may be used. A preferred embodiment of the invention involves a process wherein a nitrogen oxide containing flow from a nitric acid production process, preferably situated nearby, is used for the destruction of ammonium ions. The non-converted nitrogen oxides are recycled to the nitric acid production process. The nitrate ions for the preparation of the hydroxylammonium salt are also obtained from the nitric acid production process, in the form of nitric acid. According to this embodiment, no absorption columns are necessary for the preparation of nitric acid in the HPO process. If desired, the circulating liquid containing ammonium ions can be supplied, for instance, through a line, to the nitric acid preparation process section, where the ammonium ion destruction step using a nitrogen oxide containing flow from the nitric acid preparation process can be carried out.

Figure 2:
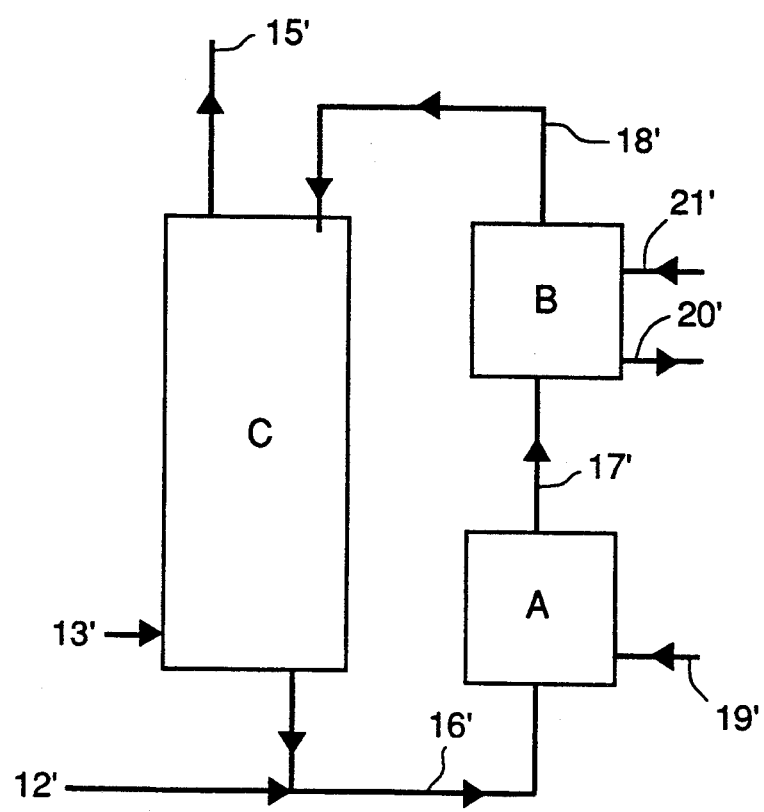
FIG. 2 shows a block diagram of a process according to the invention.

For comparison purposes, the process according to the prior art and a preferred embodiment of the process according to the invention are illustrated, respectively, in FIGS. 1 and 2, which figures are for illustrative purposes only and do not restrict the scope of the invention.

FIG. 1 and the description thereof are derived from United Kingdom 1,287,303. In FIG. 1 the nitric acid and nitrogen oxide production is represented by an ammonia combustion facility 3 equipped with a platinum gauze 4 and steam pipes 5, a hot gas condenser 6, oxidation column 8, absorption system 9, which in general comprises several columns, and stripping column 10. Nitric acid and a nitrogen oxide containing gas flow leave this section via line 12 and line 13, respectively, while oxygen, ammonia and secondary air are supplied via lines 1, 2 and 11, respectively.

The hydroxylammonium salt synthesis zone is represented by zone A, to which hydrogen is supplied via line 19. An oxime synthesis zone B where the oximation reaction and the oxime extraction take place has a supply line 21 for the ketone (cyclohexanone) and an outlet 20 for the oxime. Line 18, absorption system 14, which will in general comprise several absorption columns and oxidation reactors and lines 16 and 17 complete the recycling system, wherein the reaction medium is recycled between zone A and zone B.

In absorption system 14 the reaction medium is contacted with nitrogen oxides (via line 13). This results in destruction of the ammonium ions and formation of nitric acid by absorption of nitrogen dioxide. The non-converted nitrogen oxides are discharged via line 15.

In a preferred embodiment according to the present invention the combustion of ammonia to nitrogen oxides is carried out at atmospheric pressure and at 850°–950° C. The ammonium ion destruction step is preferably carried out at a temperature of 70°–90° C. The preparation of nitric acid by absorption of nitrogen dioxide in an aqueous solution will preferably be carried out at a temperature below 25° C. United Kingdom 1,287,302, the complete disclosure of which is incorporated herein by reference, contain an extensive description of the process conditions. The process conditions in the oxime synthesis zone (zone B) are described in United Kingdom 1,279,527, the complete disclosure of which is incorporated herein by reference. The process conditions in the hydroxylammonium salt synthesis zone (zone A) are described in U.S. Pat. No. 3,514,259, the complete disclosure of which is incorporated herein by reference.

The process flows in FIG. 2 are comparable with those in FIG. 1 and are indicated with an apostrophe. Via line 13' a nitrogen oxide containing gas flow is supplied from a nearby nitric acid production facility. Nitric acid is supplied from the nitric acid production facility via line 12'. The hydroxylammonium salt synthesis zone A' and the oxime synthesis zone B' are the same as described above. Line 18', ammonium ion destruction zone C, which will in general consist of one reactor, and lines 16' and 17' complete the recycling system, wherein the reaction medium is recycled between zone A' and zone B'.

In an ammonium ion destruction zone the reaction medium, supplied via line 18', is contacted with the nitrogen oxide containing gas flow which is supplied via line 13', at a temperature which is preferably between 70° and 90° C. Via line 15' the residual gas flow, which still contains nitrogen oxides, is fed back to the nitric acid production process. Make-up nitric acid is supplied to the recycle mixture.

The invention will be further elucidated by means of the following example, without being restricted thereto.

Example I

This example is carried out in accordance with a process as represented in FIG. 2.

Via line 13, 874 kg/h nitrogen oxides (dry) is drawn from a nitric acid plant and used for the destruction of ammonium ions in zone C. The nitrogen dioxide/nitrogen monoxide ratio is 4:1. Via line 12', 9400 kg/h HNO$_3$ (on a dry basis) is drawn from the nitric acid plant and added to the reaction medium in line 16'. The residual production of the nitric acid production process amounts to 43,000 kg/h HNO$_3$ (dry).

The efficiency of the ammonia combustion of the nitric acid production process is 96% (mol NH$_3$ converted into nitrogen oxides).

What is claimed is:

1. A process for producing hydroxylammonium salt solution, wherein an aqueous acid reaction medium which contains ammonia ions is continuously circulated between an hydroxylammonium salt synthesis zone and an oxime synthesis zone comprising the steps of:
 (i) continuously supplying nitrate ions or nitrogen oxides to be converted into nitrate by a nitrogen source to said aqueous acid reaction medium for formation of hydroxylammonium salt;
 (ii) catalytically reducing said nitrate ions with molecular hydrogen to hydroxylamine, wherein ammonium ions are formed as a by-product in reduction of said nitrate ions;
 (iii) removing said ammonium ions by conversion with nitrogen oxides by contacting said aqueous acid reaction medium with a gas flow containing 0.01 to 5 wt. % of the nitrogen oxides formed in catalytic combustion of ammonia;
 (iv) utilizing remaining nitrogen oxide containing gas flow formed in said catalytic combustion of ammonia for preparation of nitric acid.

2. The process according to claim 1, wherein non-converted nitrogen oxides of the nitrogen oxide containing gas flow in step (iv) are recycled into a process for nitric acid production, said process for nitric acid production being the source for said nitrate ions used for formation of hydroxylammonium salt.

3. The process according to claim 1, wherein preparation of nitric acid is achieved by a commercial nitric acid production process having a capacity of 200 to 750 kt $HNO_3$/year (dry).

4. The process according to claim 1, wherein 0.5–3 wt. % of said nitrogen oxides formed in the combustion effects conversion of ammonium ions into nitrogen.

5. The process according to claim 1, wherein in step (i) nitrate ions in the form of nitric acid are continuously supplied.

* * * * *